United States Patent
Hayakawa et al.

(10) Patent No.: US 8,268,225 B2
(45) Date of Patent: Sep. 18, 2012

(54) MEDICAL DEVICE MANUFACTURING METHOD AND MEDICAL DEVICE ASSEMBLY

(75) Inventors: Koichi Hayakawa, Kanagawa-ken (JP); Yukio Imai, Yamanashi-ken (JP); Shingo Ishii, Yamanashi-ken (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 26 days.

(21) Appl. No.: 12/890,865

(22) Filed: Sep. 27, 2010

(65) Prior Publication Data

US 2011/0071501 A1    Mar. 24, 2011

Related U.S. Application Data

(63) Continuation of application No. PCT/JP2009/055960, filed on Mar. 25, 2009.

(30) Foreign Application Priority Data

Mar. 27, 2008   (JP) ................................. 2008-084232

(51) Int. Cl.
*H01J 37/30* (2006.01)
(52) U.S. Cl. ......... 264/485; 264/479; 425/393; 425/174
(58) Field of Classification Search ................. 264/479, 264/485; 425/393, 174
See application file for complete search history.

(56) References Cited

U.S. PATENT DOCUMENTS

| | | | | |
|---|---|---|---|---|
| 4,490,314 A | * | 12/1984 | DuPont et al. | 264/485 |
| 5,087,394 A | * | 2/1992 | Keith | 264/470 |
| 5,409,644 A | * | 4/1995 | Martin et al. | 264/479 |
| 2008/0075628 A1 | * | 3/2008 | Judd et al. | 422/22 |
| 2009/0200697 A1 | * | 8/2009 | Aulick et al. | 264/213 |

FOREIGN PATENT DOCUMENTS

| | | |
|---|---|---|
| JP | 1-300957 A | 12/1989 |
| JP | 4-300926 A | 10/1992 |
| JP | 4-371157 A | 12/1992 |
| JP | 8-57035 A | 3/1996 |

OTHER PUBLICATIONS

International Search Report (PCT/ISA/210) issued on Jun. 23, 2009, by Japanese Patent Office as the International Searching Authority for International Application No. PCT/JP2009/055960.
Roustam Aliev, "Effect of dose rate and oxygen on radiation crosslinking of silica filled fluorosilicone rubber", Radiation Physics and Chemistry 56, 1999 (month unknown), pp. 347-352, Mexico.

* cited by examiner

*Primary Examiner* — Joseph Del Sole
*Assistant Examiner* — David N Brown, II
(74) *Attorney, Agent, or Firm* — Buchanan Ingersoll & Rooney PC

(57) ABSTRACT

A medical device in which a part to be secondarily shaped comprises a molded silicone rubber article is subjected to heatless shaping by irradiation with electron-rays. The irradiation with electron-rays enables shaping and, furthermore, sterilization under some conditions. In a medical device comprising a part in which at least a silicone rubber is used and the mechanical properties of the silicone rubber preferentially appear, the shape of the above-described part upon molding is deformed with the use of a correcting member to a level exceeding the desired deformed shape and maintained in this state. Next, electron-ray irradiation is conducted in this state and then the correcting member is eliminated. Thus, the desired deformed shape intermediate between the shape upon the molding and the shape upon the electron-ray irradiation can be obtained.

8 Claims, 1 Drawing Sheet

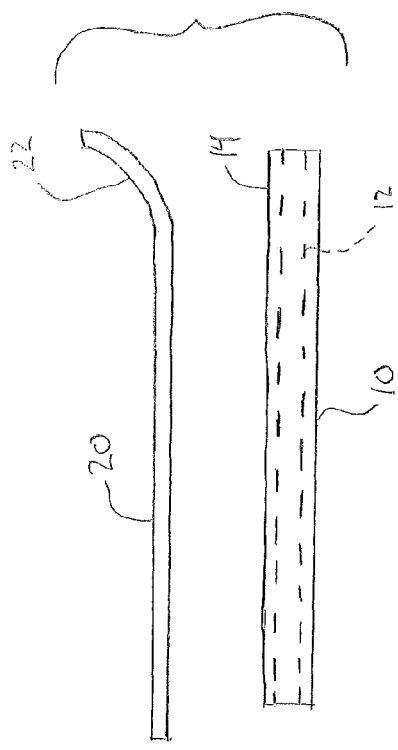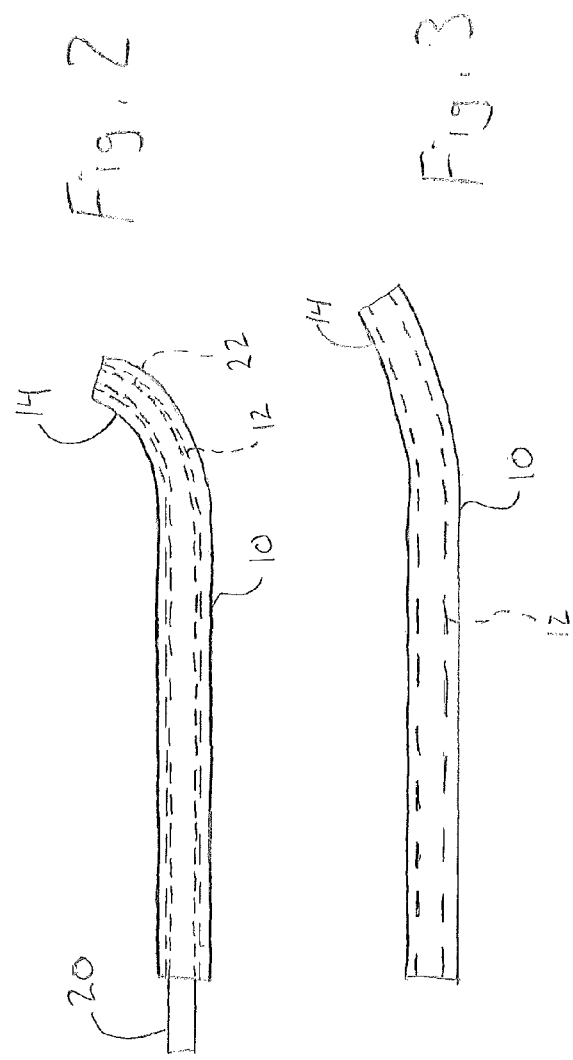

MEDICAL DEVICE MANUFACTURING METHOD AND MEDICAL DEVICE ASSEMBLY

This application is a continuation of International Application No. PCT/JP2009/055960 filed on Mar. 25, 2009, and claims priority to Japanese Application No. 2008-084232 filed on Mar. 27, 2008, the entire content of both of which is incorporated herein by reference.

TECHNICAL FIELD

The present invention generally pertains to a medical device. More specifically, the invention relates to a medical device having an insertion part configured to be inserted into a body cavity such as a blood vessel, a digestive canal, a bile duct or the like, with the insertion part being formed of silicone rubber into a fixed shape suitable for the insertion by use of an electron beam.

In general, the insertion part of the medical device is a tube or rod-like elongate body and uses the tube whose portion, e.g., distal end is shaped in angular fashion, such as in arcuate, wavy, dogleg, or L-shaped fashion. This shaping is performed by electron beam irradiation.

In particular, the medical device and method disclosed here allow for shape-fixation of the medical device concurrently with electron beam sterilization.

BACKGROUND DISCUSSION

Generally, a body cavity insertion device such as a catheter or the like is such that recently electron beam irradiation has attracted attention in view of an installation aspect and management aspect as well as an easy handling aspect in place of EOG (ethylene oxide gas) sterilization before use.

A silicon rubber tube and radioactive sterilization of such tube are known from Japanese Patent Laid-open No. Hei 4-371157. If silicon tubes that are twice-folded or four-times folded and packaged are sterilized, a phenomenon often occurs in which the silicon tubes adhere to each other. For this reason, it is considered that the radioactive irradiation cannot be used for tube sterilization. To solve such a problem, unpackaged tubes are previously irradiated with a radioactive beam such as an electron beam before sterilizing the packaged tubes. In the previous irradiation, tubes are put in a previous-irradiation tray provided inside with partitions or the like to prevent the tubes from coming contacting each other. Then, a radioactive ray irradiation device is used to emit radioactive rays to the tray to apply an energy of 2.5 to 20 Mrad thereto. This removes the residual monomer and oligomer for stabilization and thereafter sterilization is performed. At the time of the sterilization, even use of radioactive rays can prevent the silicon tubes from adhering to each other. Japanese Patent Laid-open No. Hei 4-371157 discloses that at the time of the sterilization, electron beams are directed, particularly, to the two-folded or four-folded silicon tubes, i.e., to the silicon tubes in contact with each other.

Tubes that are inserted and indwelled into a blood vessel, a digestive canal or a ventral cavity may use silicone rubber chemically stable and superior in chemical resistance in some cases. However, the silicone rubber is not a thermoplastic resin and so posterior processing such as angular-shaping may be difficult to pursue periphery-reaching performance. Generally, the shaping of medical tubes includes injection-molding silicone rubber by use of a mold with a predetermined shape, and deforming an extruded tube into a predetermined shape and then subjecting the deformed tube to heat fixation.

The present inventors started a study while considering that a reduction in step and time and simplification of an installation can be achieved if sterilization of a medical device using silicone rubber by radioactive ray irradiation and shaping of the medical device can be performed simultaneously with each other.

Japanese Patent Laid-open No. Hei 4-371157 describes only that radioactive rays are emitted two times in order to prevent the adhesion of silicone rubber tubes and to sterilize them and that the tubes are four-folded for sterilization. However, Japanese Patent Laid-open No. Hei 4-371157 nowhere discusses performing intentional shaping and using an electron beam irradiation technique for the same.

Japanese Patent Laid-open No. Hei 4-371157 mentions that what can be emitted to the silicon tube may be not only electron beams but also radioactive rays.

The inventors first deformed silicone rubber in a forcible manner and emitted gamma beams to the silicone rubber remaining deformed. However, after removing the forcible manner of deformation, the silicone rubber returned to the shape before the irradiation.

The inventors next deformed silicone rubber in a forcible manner and emitted electron beams to the silicone rubber remaining deformed. In this case, upon removing the forcible manner of deformation, the inventors discovered that the silicone rubber remained deformed. In this way, the inventors developed the medical device and method disclosed here.

A medical device whose portion to be shaped is made of a silicone rubber molded article could not be stably shaped through use of a heating device. EOG (ethylene oxide gas) sterilization, which represents one sterilization not utilizing heat, raised a concern about an influence of residual gas on a living body. To eliminate the concern, the portion to be shaped was irradiated with gamma beams and electron beams for shaping without heating. In this case, it has been found that the portion to be shaped is not shaped by gamma beams but can be shaped and also sterilized by electron beams depending on conditions.

SUMMARY

One aspect disclosed here involves a method of manufacturing a medical device having a predetermined shape portion comprising at least silicone rubber, in which a property of the silicone rubber preferentially appears and which results from being subjected to electron beam irradiation. The method comprises bringing a correcting member into contact with a medical device possessing a portion having a shape different from a shape of the predetermined shape portion, with the portion of the medical device being made of silicone rubber, and the correcting material being formed of a material not adhering, sticking or cross-linking to the silicone rubber upon contact of the correcting member with the portion made of silicone rubber, wherein the correcting member has a shape-giving shape which gives a shape to the medical device, with the shape-giving shape being different from the shape of the predetermined shape portion and different from the shape of the medical device before the correcting member is brought into contact with the medical device, and wherein the medical device and the correcting member constitute a medical device assembly. The method further involves irradiating the portion of the medical device assembly with an electron beam, and removing the correcting member from the medical device whereby the portion of the medical device possesses the shape of the predetermined shape portion.

According to another aspect, a medical device assembly with a medical device having a predetermined shape portion which uses at least silicone rubber, and in which a property of the silicone rubber preferentially appears and which results from being subjected to electron beam irradiation, wherein a correcting member which is formed of a material not adhering, sticking or cross-linking to the silicone rubber due to contact therewith, and which has a shape-giving shape further deformed from a predetermined shape of the predetermined shape portion, is in contact with the medical device, and in this contact state, the medical device which is subjected to electron beam irradiation and from which the correcting member is removed has the predetermined shape different from a shape in a free state during electron beam non-irradiation.

The method can involve use of silicone rubber having a Shore A hardness of 15 to 80 before electron beam irradiation.

The manufacturing method or medical device assembly more preferably include silicone rubber having a Shore A hardness of 25 to 90 before electron beam irradiation.

The correcting member can be a shaped (inclusive of wire-like) body or rod (inclusive of rod-like) body.

The correcting member can be a shaped cylindrical body or groove.

The correcting member can be part of a packaging body of the medical device. The packaging body can include a tray, a case, a bag, etc, with the correcting body being a part of a tray, for example, and the part works a portion for holding the medical device (e.g., a channel, a dent, a protuberance). The medical device and correcting body can be packaged together or the correcting body can be packaged by itself.

The electron beam irradiation is preferably performed to sterilize the medical device.

The shape of the predetermined shape portion is preferably a tube or a cylindrical body.

The shape of the predetermined shape portion is an elongate body such as a wire-like body or a rod-like body.

According to another aspect, a medical device assembly comprises: a medical device possessing a predetermined portion comprising silicone rubber, where the predetermined portion possesses a first shape and is adapted to be electron beam irradiated to change the first shape of the predetermined portion and cause the predetermined portion to possess a predetermined shape; and a correcting member configured to contact the predetermined portion of the medical device to form a medical device assembly which is subject to the electron beam irradiation. The correcting member is formed of a material which does not stick, adhere or cross-link to the silicone rubber when the correcting member contacts the medical device, wherein the correcting member possesses a shape-giving shape which alters the first shape of the predetermined portion of the medical device when the correcting member contacts the predetermined portion so the predetermined portion of the medical device exhibits a second shape different from the first shape, with the correcting member being moved out of contact with the predetermined portion of the medical device after the electron beam irradiation, whereupon the predetermined portion of the medical device possesses the predetermined shape which is different from the first shape and the second shape.

A medical device in which at least a portion using silicone rubber is molded into a predetermined shape by electron beam irradiation, wherein a correcting member which does not adhere, stick or cross-link to the silicone rubber in a contact state with the silicone rubber, and which holds the medical device in a bending state greater than a bending state of the predetermined shape, and the medical device constitutes a medical device assembly, and the medical device assembly is subjected to a processing amount of electron beam irradiation.

Utilizing the method disclosed here, it is possible to impart a shape to a silicone rubber molded article by posterior processing, with only modifying the shaping step being required. Therefore, the step is relatively simple, a variety of shapes can be enabled, and costs can be reduced.

Also sterilization can be performed depending on a dose of electron beam, which not only can reduce steps and time but also electron beam irradiation is required only one time. Thus, economic efficiency is relatively high.

The medical tube disclosed here does not keeps or maintain the shape produced when the tube is molded, but a shape between the shape produced when the tube is molded and a corrected shape. Therefore, the deformed process portion keeps its shape under a delicate balance between extension and compression, and is responsively varied by delicate external force to undergo restoring force. Thus, it is superior in periphery-reaching performance into a body cavity because it exhibits softness.

BRIEF DESCRIPTION OF DRAWING FIGURES

FIG. 1 is a plan view of a medical device and correcting member together forming a medical device assembly before the correcting member is brought into contact with the medical device.

FIG. 2 is a plan view of the medical device and correcting member together forming a medical device assembly after the correcting member is brought into contact with the medical device.

FIG. 3 is a plan view of the medical device after the correcting member is moved out of contact with the medical device.

DETAILED DESCRIPTION

The disclosure here relates to shape-fixation of a medical device used in a structure by electron beam irradiation, and shape fixation of a silicone rubber portion by electron beam irradiation, wherein the properties of the silicone rubber are exhibited. To provide an example of this reference to the properties of the silicone rubber being exhibited, if the silicone rubber is used together with, for example, a relatively thick or large dimensioned metal wire (e.g., a wire made of titanium), the shape of the composite article (the silicone rubber and the metal wire) depends on the shape of the metal wire because it is the properties of the metal wire which exhibit themselves. On the other hand, if the silicone rubber is used together with, for example, a relatively thin or small dimensioned metal wire, the shape of the composite article depends on the shape of the silicone rubber because the properties of the silicone rubber preferentially appear or exhibit themselves. The method disclosed here is useful in shaping hollow distal tips of catheters such as a urinary catheter, a peritoneal catheter, a feeding catheter, a venous catheter and the like, shaping of a blood vessel model (a blood vessel model used to, for example, to practice surgery), forming a complicated blood vessel path, appropriately forming or configuring a balloon to effect the folding tendency of the balloon, and shaping the distal tip of a solid rod such as a guide wire and a catheter of a ultrasonograph.

The structure which uses silicone rubber and in which the properties of silicone rubber preferentially appear here is a multilayered body made of silicone rubber and other resin or thin film metal if the structure is a hollow body like a tube. In addition, the structure is such that a layer other than the silicone rubber layer is very thin and the properties of the silicone rubber are dominant. Even if the structure is a rod-like body and the front surface of the rod-like body of silicone rubber is formed of resin or a metal thin layer which is another material, it needs only the properties of silicone rubber appearing.

Silicone rubber used here has a Shore A hardness of 15 to 80 before electron beam irradiation. Generally speaking, if the silicone rubber has a Shore A hardness less than 15, it is difficult to shape because it is too soft, and if the Shore A hardness exceeds 80, such silicone rubber is not preferable because a distal end to be inserted into a body cavity is too hard in relation to the hardness after shaping.

Silicone rubber increases in hardness after electron beam irradiation. Respective pieces of silicone rubber having Shore A hardness of 20 (NuSil LLC., silicon MED-4020), 35 (the same company, silicon MED-4035) and 50 (the same company, silicon MED-4050), which have equal intervals therebetween, before irradiation, are increased to approximately 12, 8 and 6 in hardness after irradiation with the same dose as they have lower hardness. Therefore, if the change in hardness is emphasized or important (i.e., if a relatively smaller change in hardness after electron beam irradiation is desired), a silicone rubber can be selected which has a hardness of 35 or greater to achieve a relatively smaller change in hardness upon electron beam irradiation. The hardness of silicone rubber can be adjusted by the dose of radiation.

Preferably, the silicone rubber shaped after electron beam irradiation has a Shore A hardness of 25 to 90. Generally speaking, silicone rubber having a Shore A hardness of less than 25 is not preferred because of relatively poor shape-maintaining performance during use. In addition, silicone rubber having a Shore A hardness in excess of 90 is not preferable because it is too hard as a distal end to be inserted into a body cavity.

If silicone rubber is formed in a hollow manner, a correcting member as a shaping jig needs to be formed of a material that does not adhere to, stick to or cross-link to the silicone rubber upon contact therewith and that exhibits a shape-giving shape further deformed in excess of the predetermined shape. That is, if it is desired that the medical device, following electron beam irradiation, possesses a predetermined shape, the correcting member used with the silicone rubber medical should possess or exhibit a shape-giving shape that exceeds the predetermined shape. By way of example, to produce a silicone rubber medical device possessing, after electron beam irradiation, a predetermined shape involving a bend portion bent at a first angle, the correcting member should possesses a shape (shape-giving shape) having a bend portion bent at a second angle greater than the first angle. In this way, after the correcting member is removed from the medical device following electron beam irradiation, the medical device will exhibit the predetermined shape having the bend portion bent at the first angle. A groove is formed of polypropylene, polyethylene, polystyrene or the like to correspond to the shape-giving shape and the silicone rubber formed in a hollow manner is received in the groove. In this way, electron beam irradiation can be performed thereon.

In a preferred embodiment, the electron beam irradiation is performed while a wire-like body, such as wire, easily subjected to bending, or a rod-like body, is inserted into the hollow portion.

The wire-like body and the rod-like body can be metal bodies such as iron, stainless steel, copper, aluminum, etc. Preferably, the front surface of the wire-like body or the rod-like body is subjected to silver plating, PTFE coating, or other processing so as to make it easy for the wire-like body or the rod-like body to be removed from the hollow portion after the shaping by the electron beam irradiation. In addition, such coating produces an effect of inhibiting or preventing the corrosion of the correcting member per se.

The correcting member used here may possess a previously imparted shape-giving shape or the correcting member used here may be deformed into the shape-giving shape after being combined with the medical device to be shaped.

Preferably, a correcting member as a shaping jig used when silicone rubber is formed in an elongate body such as a rod-like body or a wire-like body is a body having a groove or a cylindrical body such as a tube that is plastically deformed by external force and maintains the shape after the removal of the external force. If the correcting member is a tube, a rod-like body of silicone rubber is inserted into the tube to deform it and the maintaining force of the tube maintains the deformation. Alternatively, an auxiliary means can be used to prevent the restoration of the tube. The tube may be previously shaped. If the correcting member is a groove, the groove is previously formed into a shaping-shape. The rod-like body is received in the groove while being bent. In this case, preferably, the rod-like body is inserted into a removable cylindrical body or received in the groove. Further, the cylindrical body or groove as a jig may be part of a packaging body or another separate from the packaging body. In this case, after the packaging, electron beam irradiation can concurrently perform sterilization and shape-fixation. If the jig is part of the packaging body, it is possible to concurrently remove also the jig when the package is opened for use.

Irradiation energy of electron beams used to process the medical device disclosed here needs sufficient intensity so it can pass through the device to be irradiated. The irradiation energy may thus be 1 to 10 MeV, preferably, 5 to 10 MeV. An irradiation dose of a predetermined amount of electron beams used to process the medical device may be 1 to 100 kGy, preferably 10 to 80 kGy, most preferably 20 to 60 kGy. Generally speaking, if the dose is less than 1 kGy, shaping may be difficult, and if the dose exceeds 100 kGy, the degradation of silicone rubber of the medical device which is an irradiation object is likely to occur. Although the irradiation of electron beams depends on the size (density) of the medical device as the irradiation object, if the medical device is relatively small, the irradiation of electron beams is performed on one side of the medical device. If the medical device is large, the irradiation of electron beams is performed on both sides of the medical device or from multiple directions of the medical device. Thus, the medical device can be relatively uniformly irradiated with electron beams.

The shaping of a part where properties of silicone rubber of the medical device preferentially appear requires electron beam irradiation in the status where the part is given a bending angle approximately 5 to 6 times an intentional bending angle. The magnification of the bending angle (the increased bending angle relative to the desired bending angle in the final product) depends on the hardness of the silicone rubber and the irradiation dose of electron beams.

For example, if silicone rubber is a cylindrical body such as a tube, a jig as a correcting body is a wire-like body, which body can be a copper wire whose surface is silver-plated. This copper wire is inserted into the tube. The tube into which the copper wire is inserted is semi-circularly wound or bent around an another rod with a radius of 3 mm and is formed into a U-shape. Electron beam irradiation is performed on the U-shaped tube into which the copper wire is inserted. After the irradiation, the copper wire is removed from the U-shaped tube, with the result that a bending shape of about 30 degrees is left. Similarly, if the copper wire-inserted tube is wound or bent around the rod to be formed in a V-shape of about 135 degrees, a bending angle after the shaping is about 25 degrees. If an angle further smaller than 25 degrees is needed, the tube wound around the rod needs only to relieve the V-shaped bending. If a bending angle further greater than 30 degrees is needed, the copper wire-inserted tube may be wound around the rod one time (360 degrees), so that both ends of the rod may become linear.

Such shaping can be done by the same means as that for the tube even if silicone rubber is a wire-like body or a rod-like body. Similarly to the tube, the bending shape encountered during the electron beam irradiation differs from that encountered when the correcting member is removed.

Such a relationship can be set by an experiment.

If an irradiation dose of electron beam is equal to or greater than 10 kGy (from ISO 11137), the same effect as electronic beam sterilization can be produced. Therefore, sterilization and shaping can concurrently be performed by irradiating electron beams to the medical device packaged together with the correcting member.

FIGS. 1-3 schematically illustrate examples of the medical device 10 and correcting member 20 according to one embodiment. The medical device 10 and correcting member 20 together constitute a medical device assembly. As shown in FIG. 1, the medical device 10 is in the form of a tubular member and possesses a through hole of a size and shape to receive the correcting member 20. In this illustrated embodiment, the distal end 14 of the medical device 10 represents the predetermined portion of the medical device 10 which is subjected to electron beam irradiation. At least the distal end 14 (predetermined portion) of the medical device 10 is comprised of silicone rubber.

The correcting member 20, which is made of a material which does not adhere, stick or cross-link to the silicone rubber upon contact of the correcting member with the predetermined portion of the medical device 10, includes a portion (bent portion) 22 possessing a shape-giving bent shape. FIG. 1 illustrates that the bent portion 22 of the correcting member 20, prior to being brought into contact with the predetermined portion 14 of the medical device 10, is more bent than the predetermined portion 14 of the medical device 10. The shape-giving shape of the bent portion 22 of the correcting member 20 is able to alter or change the shape of the predetermined portion 14 of the medical device 10 when the correcting member contacts the predetermined portion 14.

FIG. 2 illustrates the portion 22 of the correcting member 20 in contact with the predetermined portion 14 of the medical device, More specifically, the correcting member 20 is positioned in the through hole 12 in the medical device 10 so that the bent portion 22 of the correcting member axially overlaps the predetermined portion 14 of the medical device 10. Comparing FIGS. 1 and 2, the shape-giving shape of the bent portion 22 of the correcting member 20 alters or changes the shape of the predetermined portion 14 so the predetermined portion of the medical device 10 exhibits a shape different from the shape of the predetermined portion 14 prior to contact with the correcting member 20.

After the correcting member 20 is in contact with the predetermined portion 14 of the medical device as shown in FIG. 2, the predetermined portion 14 of the medical device made of silicone rubber is electron beam irradiated. Thereafter, as shown in FIG. 3, the correcting member is moved out of contact with the medical device (the correcting member is removed from the through hole in the tubular member 14). The predetermined portion 14 of the medical device now exhibits a shape that is less bent than in the state shown in FIG. 2, but more bent than the state shown in FIG. 1. Thus, the predetermined portion 14 of the medical device, following electron beam irradiation and removal of the correcting member 20, possesses a shape intermediate the original shape of the predetermined portion 14 of the medical device 10 (FIG. 1) and the shape of the predetermined portion 14 when in contact and shape-influenced by the correcting member (FIG. 2). Similarly, the predetermined portion 14 of the medical device, following electron beam irradiation and removal of the correcting member 20, possesses a shape intermediate the original shape of the predetermined portion 14 of the medical device 10 (FIG. 1) and the shape of the bent portion 22 of the correcting member (FIG. 2).

The method, medical device and medical device assembly disclosed here are described in detail with reference to specific embodiments discussed below.

<First Embodiment>

A tube having an external diameter of 4 mm and an internal diameter of 2 mm was molded using silicone rubber SR-1554 (Shore A hardness 55±5) of Tigers Polymer Corporation. This molded article was cut into a length of 10 cm. Copper wire whose surface is silver-plated, having a diameter of 1.9 mm, was cut into a length of 10 cm, and was used as a shaping core.

Next, the core as a correcting member was inserted into the silicone rubber tube. The core-inserted tube was wound or bent around a rod-like body to possesses a U-turn while centering the longitudinal-axial central portion thereof. The core-inserted tube was bent at 180 degrees. In this case, the central portion of the silicone rubber tube into which the core is inserted had a bending radius of 3 mm.

Next, Belgium IBA-made Rhodotron TT-200 was used as an electron irradiation apparatus to irradiate the bent tube with an electron beam of an irradiation energy of 10 MeV, a dose of 27.5 kGy from one side, and a dose of 27.5 kGy from the other side, 55.0 kGy in total.

Next, the core was removed from the bending tube, and thereafter the bending angle of the tube relative to the longitudinal axis thereof was measured, with the result that it was 30 degrees.

<Second Embodiment>

The silicone rubber tube into which the core was inserted in the first embodiment was hooked onto the rod-like body and bent in a V-shape at 135 degrees with respect to the longitudinal axis. In this case, the central portion of the silicone rubber tube into which the core was inserted had a bending radius of 3 mm.

Next, the same electron irradiation apparatus as in the first embodiment was used to emit an electron beam at the bent tube under the same conditions.

Next, after the core was removed from the bent tube, a bending angle relative to the longitudinal axis of the tube was measured, with the result that it was 25 degrees.

<Comparative Examples 1 to 4>

First and second comparative examples were obtained by the same procedures as in the first and second embodiments, respectively, without the electron beam irradiation. The bent tubes after the removal of the cores (wires) had no bending tendency (i.e., the tube was no longer bent after removing the core).

Third and fourth comparative examples were obtained by the same procedures as in the first and second embodiments, respectively, and by gamma beam irradiation in place of the electron beam irradiation. Bent tubes after the removal of cores in the third and fourth comparative examples had no bending tendency.

<Third Embodiment>

A tube having an external diameter of 3.5 mm and an inner diameter of 2 mm was molded using silicone rubber with the same grade number as in the first embodiment.

The tube was bent at 180 degrees with respect to a longitudinal axis by use of the core similarly to the first embodiment.

Thereafter, the bent tube was irradiated with an electron beam in the same procedure as in the first embodiment and the core was removed from the tube. The bending angle of the tube relative to the longitudinal axis was measured, with the result that it was 32 degrees.

<Fourth Embodiment>

Similarly to the third embodiment, the silicone rubber tube of the third embodiment into which the core was inserted was subject to electron beam irradiation with the exception that it was bent at 135 degrees.

Next, after the core was removed from the bent tube, the bending angle of the tube with respect to the longitudinal axis was measured, with the result that it was 23 degrees.

<Comparative Examples 5 to 8>

Fifth and sixth comparative examples were obtained by the same procedures as in the third and fourth embodiments, respectively, without the electron beam irradiation. A silicone rubber tube bent at 180 degrees had a bending tendency of as slight as three degrees after the removal of the core. On the other hand, a silicone rubber tube bent at 135 degrees had no bending tendency (i.e., the tube was no longer bent after removing the core).

Seventh and eighth comparative examples were obtained by the same procedures as in the third and fourth embodiments, respectively, and by gamma beam irradiation in place of electron beam irradiation. Silicone rubber tubes after the removal of corresponding cores had slight bending tendency.

<Fifth Embodiment>

A tube having an external diameter of 4.5 mm and an internal diameter of 3 mm, made of silicone rubber 3×4.5CR (Shore A hardness 65 to 70) of Shin-Etsu Polymer Co., Ltd. was prepared.

The tube was bent at 180 degrees with respect to a longitudinal axis by use of the core similarly to the first embodiment.

Thereafter, in the same procedure as in the first embodiment, the bent tube was subjected to the electron beam irradiation and the core was removed therefrom. The bending angle of the tube relative to the longitudinal axis thereof was measured, with the result that it was 33 degrees.

<Sixth Embodiment>

A silicone rubber tube was subjected to electron beam irradiation similarly to the third embodiment with the exception that the silicone rubber tube of the fifth embodiment into which the core was inserted was bent at 135 degrees with respect to the longitudinal axis.

Next, after the core was removed from the bent tube, the bending angle of the tube relative to the longitudinal axis was measured, with the result that it was 24 degrees.

<Comparative Examples 9 to 12>

Ninth and tenth comparative examples were obtained by the same procedures as in the fifth and sixth embodiments, respectively, without the electron beam irradiation. A silicone rubber tube bent at 180 degrees had a bending tendency of as slight as four degrees after the removal of the core. On the other hand, a silicone rubber tube bent at 135 degrees had no bending tendency (i.e., the tube was no longer bent after removing the core).

Eleventh and twelfth comparative examples were obtained by the same procedures as in the fifth and sixth embodiments, respectively, and by gamma beam irradiation in place of electron beam irradiation. Silicone rubber tubes after the removal of corresponding cores had slight bending tendency.

Using silicone rubber having a Shore A hardness of 20, 35 and 50, the same evaluation as the above embodiments and comparative examples was performed. This evaluation involved the bending angle, the presence or absence of the electron beam irradiation and the gamma beam irradiation studied in the first through sixth embodiments and the first through twelfth comparative examples. These studies show the same tendencies as the embodiments and comparative examples described above regarding the presence or absence of the electron beam irradiation. The above embodiments and comparative examples describe the use of silicone rubber tubes. By using, as a correcting member, a polypropylene-made tray having a groove corresponding to the intended shape-giving shape, a silicone rubber-made wire-shaped or rod-shaped body was fitted in the groove and shaped by electron beam irradiation. Such shaping was studied. The results of this study show the same tendency as discussed above.

A thin film cylindrical body such as a balloon is different, as below, from a catheter tube which is even the same cylindrical body. In a state in which the balloon is deflated, two blades, three blades or four blades of the balloon are formed to project outwardly from the central shaft of the balloon. A polypropylene sheet-made correcting member is interposed among the blades. The correcting member and the blades are wound along the central shaft of the balloon or further, the blades are covered from above (outside) by a correcting member or a thermal shrinking tube as a shape-fixation member. Then, they are subjected to electron beam irradiation. In this way, the silicone rubber-made balloon can be given the shape. Thus, the shape in the state of the balloon is deflated can be given.

Incidentally, the Shore A hardness uses list values and the measurement values of TECLOCK Co., Ltd. made GS-719N "Type A Duro-meter."

The detailed description above describes embodiments of the medical device and manufacturing method disclosed here. The invention is not limited, however, to the precise embodiment and variations described and illustrated above. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A method of manufacturing a medical device having a predetermined portion which possesses a predetermined shape and which comprises silicone rubber, the method comprising;

bringing a correcting member into contact with the predetermined portion of a medical device, the predetermined portion of the medical device comprising the silicone rubber possessing a first shape, the correcting member being formed of a material which does not adhere, stick or cross-link to the silicone rubber upon contact of the correcting member with the predetermined portion of the medical device comprising the silicone rubber, the correcting member possessing a shape-giving shape which alters the first shape of the predetermined portion of the medical device so that the predetermined portion of the medical device possesses a shape different from the first shape and different from the predetermined shape;

irradiating the predetermined portion of the medical device with an electron beam while the correcting member is in contact with the predetermined portion of the medical device; and moving the correcting member out of contact with the medical device, with the predetermined portion of the medical device possessing the predetermined shape after the correcting member is moved out of contact with the predetermined portion.

2. The method of manufacturing a medical device according to claim 1, wherein the medical device it a tubular member possessing a through hole, the contacting of the medical device with the correcting member comprising positioning the correcting member in the through hole of the tubular member, and the moving of the correcting member out of contact with the tubular member comprising removing the correcting member from the through hole in the tubular member.

3. The method of manufacturing a medical device according to claim 2, wherein the tubular member possesses a distal end portion and a proximal end portion, the predetermined portion being the distal end portion of the tubular member.

4. The method of manufacturing a medical device according to claim 1, wherein the silicone rubber has a Shore A hardness of 15 to 80 before electron beam irradiation.

5. The method of manufacturing a medical device according to claim 1, wherein the correcting member is a shaped wire body or a shaped rod body.

6. A medical device manufacturing method in which at least a predetermined portion of the medical device made is molded into a predetermined bending shape by electron beam irradiation, the method comprising:

bringing a correcting member into contact with the predetermined portion of the medical device, the predetermined portion of the medical device comprising silicone rubber, the correcting member not adhering, sticking or cross-linking to the silicone rubber when the correcting member is in contact with the silicone rubber of the predetermined portion even when the correcting member and the silicone rubber are subjected to an amount of electron beam irradiation while the correcting member is in contact with the silicone rubber, the contact of the correcting member with the predetermined portion bending the predetermined portion of the medical device into a first bending state that is more bent than the predetermined portion before contact with the correcting member and holding the predetermined portion in the bending state; and electron beam irradiating the predetermined portion of the medical device.

7. The method of manufacturing a medical device according to claim 6, wherein the medical device is a tubular member, wherein the bringing the correcting member into contact with the predetermined portion of the medical device comprises inserting the correcting member in a through hole in the tubular member, and further comprising removing the correcting member from the through of the tubular member after electron beam irradiating the predetermined portion of the medical device, whereby the predetermined portion of the tubular device possesses a second bending state after removing the correcting member, the predetermined portion being less bent in the second bending state than in the first bending state.

8. The method of manufacturing a medical device according to claim 6, wherein the medical device is a tubular member which possesses a distal end portion and a proximal end portion, the predetermined portion being the distal end portion of the tubular member.

* * * * *